United States Patent
Yasunaga et al.

(10) Patent No.: US 11,529,496 B2
(45) Date of Patent: Dec. 20, 2022

(54) MEDICAL ASSISTANCE DEVICE

(71) Applicant: TERUMO KABUSHIKI KAISHA, Tokyo (JP)

(72) Inventors: Mitsuteru Yasunaga, Shizuoka (JP); Kohtaroh Kusu, Shizuoka (JP); Atsushi Nomura, Tokyo (JP); Yusuke Sekine, Kanagawa (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 0 days.

(21) Appl. No.: 16/939,365

(22) Filed: Jul. 27, 2020

(65) Prior Publication Data
US 2020/0353214 A1    Nov. 12, 2020

Related U.S. Application Data

(63) Continuation of application No. PCT/JP2018/034993, filed on Sep. 21, 2018.

(30) Foreign Application Priority Data

Feb. 7, 2018    (JP) ............................. JP2018-020553

(51) Int. Cl.
| | |
|---|---|
| *A61M 25/01* | (2006.01) |
| *A61M 25/09* | (2006.01) |
| *A61M 5/00* | (2006.01) |

(52) U.S. Cl.
CPC .. *A61M 25/0113* (2013.01); *A61M 25/09041* (2013.01); *A61M 5/007* (2013.01); *A61M 2205/332* (2013.01); *A61M 2205/3327* (2013.01)

(58) Field of Classification Search
CPC ........ A61M 25/0113; A61M 25/09041; A61M 2205/332; A61M 25/02; A61M 25/09; A61M 2205/3327; A61M 25/01
See application file for complete search history.

(56) References Cited

U.S. PATENT DOCUMENTS 3,995,628 A * 12/1976 Gula .................... A61M 25/065
                                                                    604/159
2003/0122021 A1     7/2003  Mcconnell et al.
(Continued)

FOREIGN PATENT DOCUMENTS

| CN | 206597189 U | 10/2017 |
| JP | S63162495 A | 7/1988 |

(Continued)

OTHER PUBLICATIONS

The extended European Search Report dated Oct. 29, 2020, by the European Patent Office in corresponding European Patent Application No. 18904745.9-1122. (7 pages).

(Continued)

*Primary Examiner* — Amber R Stiles
*Assistant Examiner* — Avery Smale
(74) *Attorney, Agent, or Firm* — Buchanan Ingersoll & Rooney PC

(57) ABSTRACT

A medical assistance device capable of improving handling or an operation of a medical device. The medical assistance device is connected to the medical device which is inserted into a biological lumen and is used in a procedure in the biological lumen. The medical assistance device includes a support, a winding unit which is rotatably provided about a support shaft with respect to the support and winds the medical device, and a connection section which is provided in the winding unit and is connected to an end portion of the medical device.

20 Claims, 7 Drawing Sheets

(56) References Cited

U.S. PATENT DOCUMENTS

| | | | |
|---|---|---|---|
| 2005/0234423 A1 | 10/2005 | Mogensen | |
| 2006/0229587 A1* | 10/2006 | Beyar | A61M 25/0113 |
| | | | 604/510 |
| 2011/0011401 A1 | 1/2011 | Skovgard | |
| 2011/0028941 A1 | 2/2011 | Nagano et al. | |
| 2013/0178836 A1 | 7/2013 | Teutsch | |
| 2013/0184805 A1* | 7/2013 | Sawada | A61M 25/0097 |
| | | | 623/1.11 |
| 2016/0008574 A1 | 1/2016 | Bencteux et al. | |
| 2016/0136391 A1* | 5/2016 | Foley | A61M 25/0111 |
| | | | 604/544 |

FOREIGN PATENT DOCUMENTS

| | | |
|---|---|---|
| JP | H0675507 U | 10/1994 |
| JP | 2005514095 A | 5/2005 |
| JP | 2005319083 A | 11/2005 |
| JP | 2016510606 A | 4/2016 |
| JP | 2017-079824 A | 5/2017 |
| WO | 2008074039 A1 | 6/2008 |
| WO | 2013/134486 A2 | 9/2013 |
| WO | 2014/135814 A1 | 9/2014 |

OTHER PUBLICATIONS

International Search Report (PCT/ISA/210) dated Oct. 30, 2018, by the Japanese Patent Office as the International Searching Authority for International Application No. PCT/JP2018/034993.

Written Opinion (PCT/ISA/237) dated Oct. 30, 2018, by the Japanese Patent Office as the International Searching Authority for International Application No. PCT/JP2018/034993.

Office Action (The First Office Action) dated Mar. 3, 2022, by the State Intellectual Property Office of People's Republic of China in corresponding Chinese Patent Application No. 201880085041.1 and an English Translation of the Office Action. (18 pages).

* cited by examiner

MEDICAL ASSISTANCE DEVICE

CROSS-REFERENCES TO RELATED APPLICATIONS

This application is a continuation of International Application No. PCT/JP2018/034993 filed on Sep. 21, 2018, which claims priority to Japanese Application No. 2018-020553 filed on Feb. 7, 2018, the entire content of both of which is incorporated herein by reference.

FIELD OF THE DISCLOSURE

The present disclosure generally relates to a medical assistance device which is connected to a medical device used in a procedure in a biological lumen.

BACKGROUND DISCUSSION

In recent years, for example, in a procedure such as a treatment or a diagnosis in a biological lumen such as a blood vessel, a bile duct, a trachea, an esophagus, or a urethra, a catheter treatment which is relatively less invasive than a surgical operation has been recommended. For example, according to a site (puncture site) where a catheter is inserted into a human body, the catheter treatment is classified into a Trans-Radial Intervention (TRI), a Trans-Femoral Intervention (TFI), or the like.

In general, a diameter of a blood vessel of a radial artery is relatively smaller than a diameter of a blood vessel of a femoral artery. Moreover, a speed of a blood flow in a blood vessel and a blood pressure in a blood vessel in the radial artery are rather different from those of the femoral artery. Therefore, compared with the Trans-Femoral Intervention, the Trans-Radial Intervention has less bleeding at the puncture site. Accordingly, in the Trans-Radial Intervention, hemostasis at the puncture site is relatively easier, and a rest time can be shortened. Therefore, according to a medical condition, a period from hospitalization to discharge can be shortened, or day surgery can be realized. In this way, the Trans-Radial Intervention can help reduce a relative physical burden or an economic burden on a patient. As a result, the Trans-Radial Intervention has been recognized as being relatively superior compared to the Trans-Femoral Intervention.

In a Percutaneous Coronary Intervention (PCI: coronary angioplasty), a thin tube called a "catheter" is inserted from a femoral artery of a lower limb, a radial artery of an upper limb, or a brachial artery and is delivered to a stenosed site of a coronary artery through an aorta. In this way, the procedure in the blood vessel of the coronary artery is performed. In this case, for example, a length of the catheter for delivering a procedure device to a procedure site such as a lesion area may be 100 cm to 110 cm. For example, a length of the procedure device may be 120 cm to 135 cm. A length of a guide wire which is used together with the catheter and the procedure device can be as long as 180 cm to 280 cm. Note that the length of each medical device is an example and may be changed according to a height and a body type of a patient.

Meanwhile, in the related art, in an Endovascular Treatment (EVT), the Trans-Femoral Intervention is adopted in a procedure in a biological lumen (peripheral blood vessel) of a lower limb. In the case of the Trans-Femoral Intervention, there are an ipsilateral approach which approaches from the same foot as a foot where a procedure site exists and a contralateral approach which approaches from the other foot opposite to the foot where the procedure site exists. For example, in the ipsilateral approach, a length of a catheter which delivers a procedure device to the procedure site can be 45 cm. For example, a length of the procedure device can be 80 cm. A length of a guide wire which is used together with the catheter and the procedure device can be as long as 180 cm. Similarly, in the contralateral approach, for example, a length of a catheter which delivers a procedure device to the procedure site can be 90 cm. For example, a length of the procedure device can be 135 cm. A length of a guide wire which is used together with the catheter and the procedure device can be as long as 260 cm.

However, even in the procedure in the biological lumen of the lower limb, when the Trans-Radial Intervention is to be adopted in consideration of a medical economy and an improvement in a Quality Of Life (QOL) of a patient, for example, it is assumed that the length of the catheter delivering the procedure device to the procedure site, for example, is 150 cm. For example, it is assumed that the length of the procedure device is 200 cm. It is assumed that the length of the guide wire which is used together with the catheter and the procedure device can be as long as 380 cm. In this way, when the Trans-Radial Intervention is to be adopted in the procedure in the biological lumen of the lower limb, the length of each medical device may not only be longer than the height of the patient or the height of a surgeon, but may also be longer than a catheter table of which an entire length in a longitudinal direction is about 330 cm. Accordingly, when the Trans-Radial Intervention is to be adopted in the procedure in the biological lumen of the lower limb, handling of the medical device can be difficult, and as a result, an operation of the medical device may be rather difficult.

Moreover, the catheter treatment is performed in a catheter room. A blood vessel imaging device (angio device), a catheter table, a digital imaging device, an electrocardiogram (polygraph), a contrast agent automatic injection device (injector), or the like is installed in the catheter room. In addition, a defibrillator, an aorta balloon pumping device, a percutaneous cardiopulmonary assist device, an extracorporeal pacemaker, a human oral breathing device, an emergency drug set, or the like is installed as necessary. Accordingly, a space where the surgeon, an assistant, or the like can work in the catheter room is not very large and is limited. Therefore, when a length of the medical device is rather long in a situation where the catheter treatment is performed in the limited space of the catheter room, the handling and the operation of the medical device may be difficult. If the handling or the operation of the medical device is rather difficult, there is a concern that the medical device may carelessly come into contact with a dirty area such as a floor of the catheter room or may come into contact with a device installed in the catheter room, a patient, the surgeon, or the like, against an intention of the surgeon or the assistant.

Japanese Patent Application Publication No. 2005-319083 discloses a winding reel including a winding member which winds an insertion portion of a treatment tool for an endoscope which is inserted into an endoscope. In the winding member of the winding reel disclosed in Japanese Patent Application Publication No. 2005-319083, a plurality of curved portions which are curved along a winding direction of the insertion portion are disposed apart from each other. When the treatment tool for an endoscope is wound by the winding reel, a portion which is wound while being curved is reduced. Moreover, a burden on the insertion portion of the treatment tool for an endoscope can be reduced.

Technical Problem

However, the winding reel disclosed in Japanese Patent Application Publication No. 2005-319083 is a device for winding the insertion portion of the treatment tool for an endoscope, and is not used in a limited narrow space such as the catheter room. In addition, it is impossible to apply the winding reel for winding the insertion portion of the treatment tool for an endoscope to a medical device used in a procedure in a thin biological lumen such as a blood vessel. Therefore, in a case where the medical device used in the procedure in the biological lumen is relatively long, it is not possible to solve a problem that the handling and the operation of the medical device is difficult only by applying the technology described in Japanese Patent Application Publication No. 2005-319083 to the medical device.

SUMMARY

A medical assistance device is disclosed, which is capable of improving the handling and the operation of the medical device.

A medical assistance device is disclosed, which is connected to a medical device which is inserted into a biological lumen and used in a procedure in the biological lumen, the medical assistance device including: a support; a winding unit which is rotatably provided about a support shaft with respect to the support and configured to wind the medical device; and a connection section which is provided in the winding unit and is connected to an end portion of the medical device.

In accordance with an aspect, the winding unit is provided rotatably about the support shaft with respect to the support. Moreover, the connection section connected to an end portion of the medical device is provided in the winding unit. That is, the winding unit is connected to the medical device via the connection section. Moreover, the winding unit can wind the medical device. Accordingly, even in a case where the medical device is relatively long, in the medical assistance device of the present disclosure, the winding unit winds the medical device, and thus, the handling or an operation of the medical device can be improved. Accordingly, the medical device can be prevented from carelessly coming into contact with a dirty area, for example, such as a floor of a catheter room or coming into contact with a device installed in the catheter room, a patient, a surgeon, or the like, against an intention of the surgeon or an assistant.

In accordance with another aspect, the winding unit has a grip portion which is rotationally operated.

In accordance with an aspect, the winding unit has the grip portion which is rotationally operated. Therefore, even in a case where electricity is not supplied, the surgeon can operate the grip portion so that the winding unit is rotated to wind the medical device.

In accordance with another aspect, the medical assistance device further includes a biasing unit which is connected to the support and the winding unit and biases the winding unit in a direction in which the medical device is wound.

In accordance with an aspect, the medical assistance device further includes the biasing unit which biases the winding unit in the direction in which the medical device is wound. Therefore, the winding unit can rather easily wind the medical device.

In accordance with another aspect, the medical assistance device further includes a lock mechanism which is provided in the support and stops a rotating operation of the winding unit biased by the biasing unit.

In accordance with an aspect, even in a case where the winding unit is biased by the biasing unit, the lock mechanism can stop the rotating operation of the winding unit. Therefore, the surgeon can perform manipulation with the medical device appropriately bent.

In accordance with another aspect, the medical assistance device further includes a rotation drive unit which is provided in the support and generates a rotation force for rotating the winding unit when a voltage is supplied to the rotation drive unit.

In accordance with an aspect, even when the winding unit is not manually operated by the surgeon, a voltage is supplied to the winding unit so that the winding unit can be automatically rotated and can wind the medical device.

In accordance with another aspect, the medical assistance device further includes a rotation detection unit which detects a rotation angle of the winding unit, and a control unit which receives a signal transmitted from the rotation detection unit and calculates a winding length and an unwinding length of the medical device from a predetermined position, based on the rotation angle detected by the rotation detection unit.

In accordance with an aspect, even in a state where at least a portion of the medical device is wound around the winding unit, the surgeon can grasp how to take a length of the medical device inserted into a body during the procedure in the biological lumen or a deflection amount (buffer amount) of the medical device based on the length calculated by the control unit.

In accordance with another aspect, based on the rotation angle detected by the rotation detection unit, the control unit is configured to control the rotation drive unit to unwind the medical device when the control unit detects a force in a direction in which the medical device is unwound, and the control unit is configured to control the rotation drive unit to wind the medical device when the control unit detects a force in a direction in which the medical device is wound.

In accordance with an aspect, the control unit can control the rotation drive unit to assist a manipulation or an operation of the surgeon unwinding or winding the medical device. Therefore, the medical assistance device according to the present disclosure can support the procedure in the biological lumen.

In accordance with another aspect, the rotation force for rotating the winding unit is a first rotation force, the rotation drive unit for generating the first rotation force is a first rotation drive unit, and a second rotation drive unit which generates a second rotation force for rotating the medical device about an axis of the medical device connected to the connection section is further provided.

In accordance with an aspect, the second rotation drive unit can generate the second rotation force and rotates the medical device about the axis of the medical device connected to the connection section. Accordingly, a choice of the procedure in the biological lumen can be broadened. For example, in a case where the medical device is an image diagnosis catheter (for example, IVUS catheter: Intra Vascular Ultra Sound catheter), the second rotation drive unit rotates the medical device about the axis of the medical device in the biological lumen, and thus, an image of a target lesion can be acquired in a circumferential direction. Alternatively, for example, in a case where the medical device is the guide wire, the second rotation drive unit rotates the medical device about the axis of the medical device in the biological lumen, and thus, it is possible to improve selectivity of a blood vessel in a bifurcated portion of the blood vessel.

In accordance with another aspect, at least one of the support and the winding unit has an introduction portion which is spatially connected to the connection section, and into which another medical device different from the medical device is inserted or a working fluid used at the time of the procedure is fed.

In accordance with an aspect, the surgeon can insert another medical device or feed the working fluid through the introduction portion. For example, in a case where the medical device is a catheter, the surgeon can insert the guide wire into a lumen of the catheter through the introduction portion. Alternatively, for example, in the case where the medical device is the catheter, the surgeon can feed the saline for priming into the lumen of the catheter through the introduction portion.

In accordance with another aspect, a medical assistance device is disclosed configured to be connected to two or more medical devices, the two or more medical devices configured to be insertable into a biological lumen and used in a procedure in the biological lumen, the medical assistance device comprising: a support; two or winding units, each of the two or more winding units rotatably provided about a support shaft with respect to the support and configured to independently wind one of the two or more medical devices; and two or more connection sections being provided in the two or more winding units and configured to be connected to an end portion of each of the two or more medical devices.

In accordance with an aspect, a medical system is disclosed, the medical system comprising: one or more medical devices, the one or more medical devices configured to be insertable into a biological lumen and used in a procedure in the biological lumen; and a medical assistance devices, the medical assistance device including a support, a winding unit which is rotatably provided about a support shaft with respect to the support and winds the medical device, and a connection section which is provided in the winding unit and is connected to an end portion of the medical device.

In accordance with another aspect, a medical assistance device is disclosed, which is capable of improving handling or an operation of a medical device.

DETAILED DESCRIPTION

Figure 1:
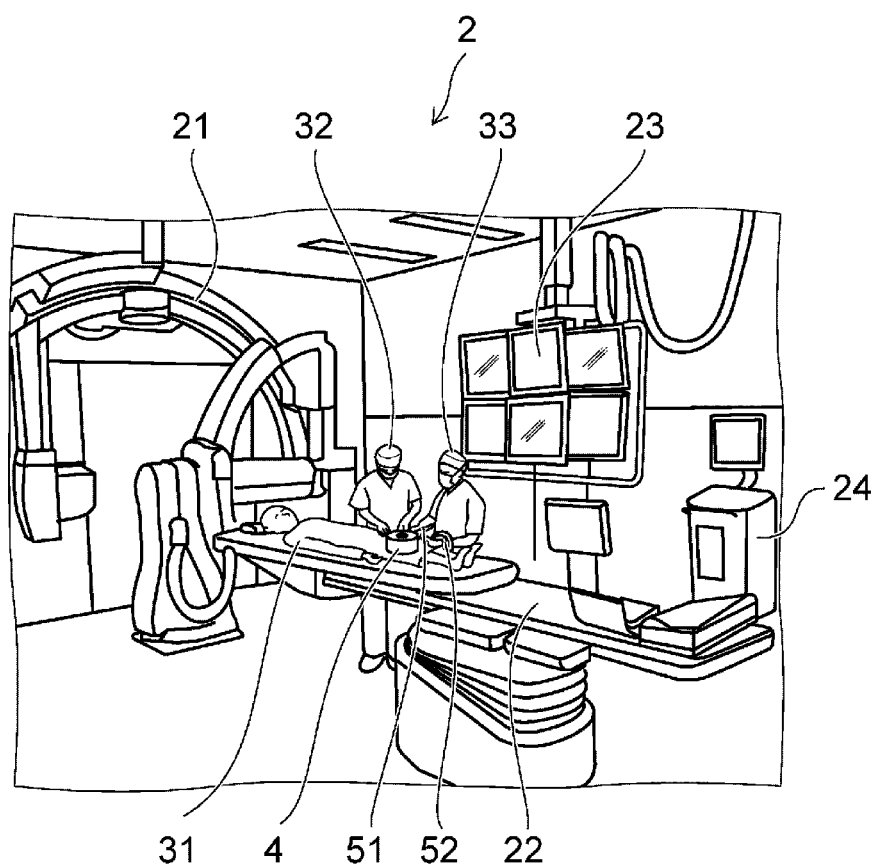
FIG. 1 is a perspective view illustrating a situation before a procedure in a catheter room in which a medical assistance device according to an embodiment of the present disclosure is installed.

Set forth below with reference to the accompanying drawings is a detailed description of embodiments of a medical assistance device which is connected to a medical device used in a procedure in a biological lumen representing examples of the inventive medical assistance device which is connected to the medical device used in a procedure in a biological lumen. Note that since embodiments described below are preferred specific examples of the present disclosure, although various technically preferable limitations are given, the scope of the present disclosure is not limited to the embodiments unless otherwise specified in the following descriptions. Moreover, in the drawings, the same reference signs are assigned to the same components, and detailed descriptions of the same reference signs assigned to the same components are appropriately omitted.

FIG. 1 is a perspective view illustrating a situation before a procedure in a catheter room in which a medical assistance device according to an embodiment of the present disclosure is installed.

Figure 2:
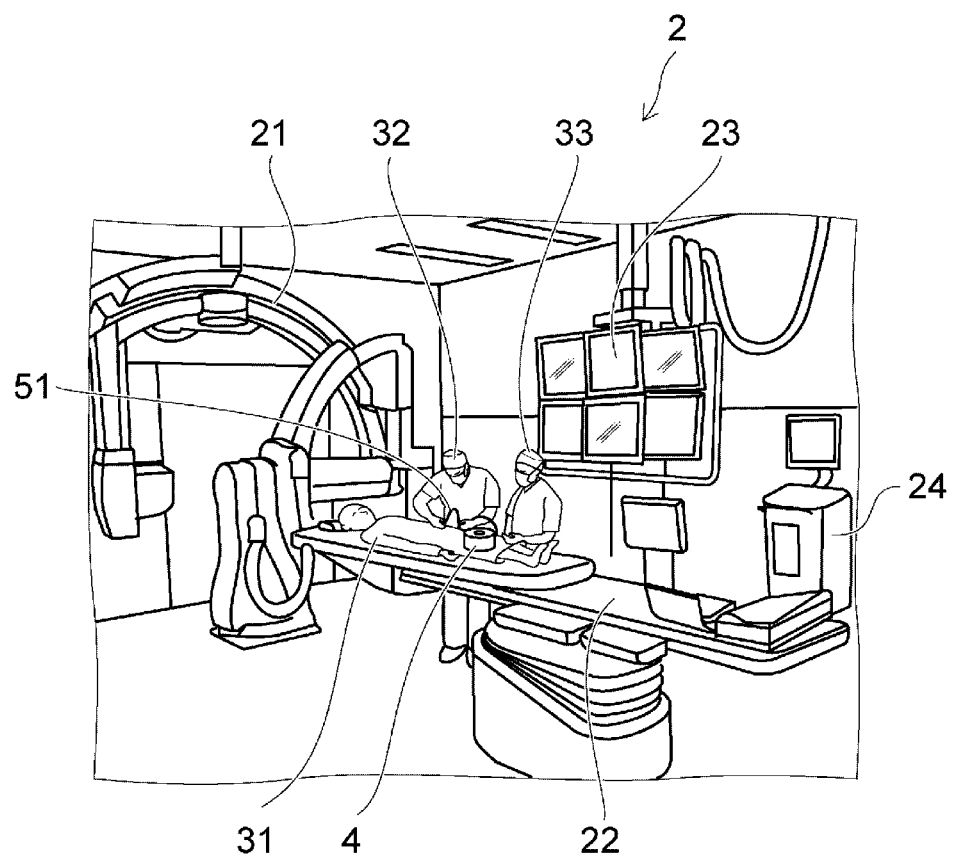
FIG. 2 is a perspective view illustrating a situation during the procedure in the catheter room in which the medical assistance device according to the present embodiment is installed.

FIG. 2 is a perspective view illustrating a situation during the procedure in the catheter room in which the medical assistance device according to the present embodiment is installed.

A medical assistance device 4 according to the present embodiment is connected to a medical device such as a catheter or a guide wire used in a procedure in a biological lumen. The medical assistance device 4 can be used regardless of a difference in manipulation in a Percutaneous Coronary Intervention (PCI: coronary angioplasty), an Endovascular Treatment (EVT), or the like and a difference in a puncture site in a Trans-Radial Intervention (TRI), a Trans-Femoral Intervention (TFI), or the like. The same applies to medical assistance devices 4A, 4B, 4C, 4D, 4E, and 4F described later with reference to FIGS. 6 to 10.

As illustrated in FIGS. 1 and 2, for example, a blood vessel imaging device (angio device) 21, a catheter table 22, a digital imaging device 23, an electrocardiogram (polygraph) 24, a contrast agent automatic injection device (injector, not illustrated), or the like is installed in a catheter room 2 in which a procedure such as a treatment or diagnosis in the biological lumen is performed using a medical device 51 such as the catheter or the guide wire. In addition, a defibrillator, an aorta balloon pumping device, a percutaneous cardiopulmonary assist device, an extracorporeal pacemaker, a ventilator, an emergency drug set, or the like is installed as necessary.

Note that in the catheter room 2 illustrated in FIGS. 1 and 2, backs (i.e., back sides) of a surgeon 32 and an assistance 33 face a monitor of the digital imaging device 23 for convenience of explanation. However, actually, in the catheter room 2, the surgeon 32 and the assistance 33 (hereinafter, referred to as a "surgeon 32 or the like" for convenience of explanation) perform the procedure while checking the monitor of the digital imaging device 23. For example, the surgeon 32 or the like moves to a position at which the monitor of the digital imaging device 23 can be checked, and performs the procedure while checking the monitor. Alternatively, for example, the surgeon 32 or the like moves the monitor to the position at which the monitor of the digital imaging device 23 can be checked, and performs the procedure while checking the monitor.

In accordance with an aspect, the blood vessel imaging device 21 has an X-ray tube which generates an X-ray and a Flat Panel Detector (FPD) which receives the X-ray transmitted through a patient 31 and converts the X-ray into image information. Moreover, the blood vessel imaging device 21 converts an X-ray image in which the X-ray transmitted through the patient 31 from the X-ray tube is attenuated by an anatomical structure of the patient 31 and a contrast agent into a digital image signal by the Flat Panel Detector (FPD) and transmits the converted digital image signal to the digital imaging device 23. The catheter table 22 is a table on which the patient 31 lays down, and a top plate portion of catheter table 22 can move up and down and move in the front-rear and left-right directions in a state where the patient 31 lays down. The digital imaging device 23 receives the X-ray image transmitted from the blood vessel imaging device 21, digitally records the X-ray image, and automatically reproduces the X-ray image on a reference monitor. Further, the digital imaging device 23 can perform slow reproduction and stillness of the X-ray image or zoom-in of a lesion area.

As described above, various devices are installed in the catheter room 2. Accordingly, a space in which the surgeon 32, the assistance 33, or the like can be active in the catheter room 2 is not relatively large and may be limited. As illustrated in FIG. 1, the surgeon 32 or the like pulls out a medical device 51 such as a catheter from a medical device holder 52 such as a catheter holder in a limited narrow space of the catheter room 2 and prepares (starts-up or sets-up) a procedure in a biological lumen. Further, as illustrated in FIG. 2, the surgeon 32 or the like operates the medical device 51 in the limited space of the catheter room 2 or operates the blood vessel imaging device 21, the catheter table 22, or the like to perform the procedure in the biological lumen.

For example, when the Trans-Radial Intervention is adopted in a procedure in a biological lumen (peripheral blood vessel) of a lower limb, a length of the medical device 51 may not only be longer than the height of the patient 31, the surgeon 32, or the like, but may also be longer than the catheter table 22 of which an entire length in a longitudinal direction may be, for example, about 330 cm. Accordingly, when the Trans-Radial Intervention is to be adopted in the procedure in the biological lumen of the lower limb, handling of the medical device 51 may be relatively difficult, and as a result, an operation of the medical device 51 may be relatively difficult.

Meanwhile, the medical assistance device 4 according to the present embodiment is connected to the medical device 51 and can wind the medical device 51. In FIGS. 1 and 2, the medical assistance device 4 is placed at or near a crotch or thigh of the patient 31, but the medical assistance device 4 may be placed anywhere on the catheter table 22. For example, the medical assistance device 4 may be fixed to a predetermined location of the catheter table 22. Alternatively, the medical assistance device 4 may be freely detachably attached to the predetermined location of the catheter table 22. The location of the medical assistance device 4 is not particularly limited.

Even in a case where the medical device 51 is relatively long, the medical assistance device 4 according to the present embodiment winds the medical device 51, and thus, can help improve the handling or operation of the medical device 51. Accordingly, it is possible to prevent the medical device 51 from carelessly coming into contact with a dirty area such as a floor of the catheter room 2 or coming into contact with a device installed in the catheter room 2, the patient 31, the surgeon 32, or the like, against an intention of the surgeon 32 or the assistant 33. Hereinafter, the medical assistance device 4 according to the present embodiment will be described in detail with reference to the drawing.

Figure 3:
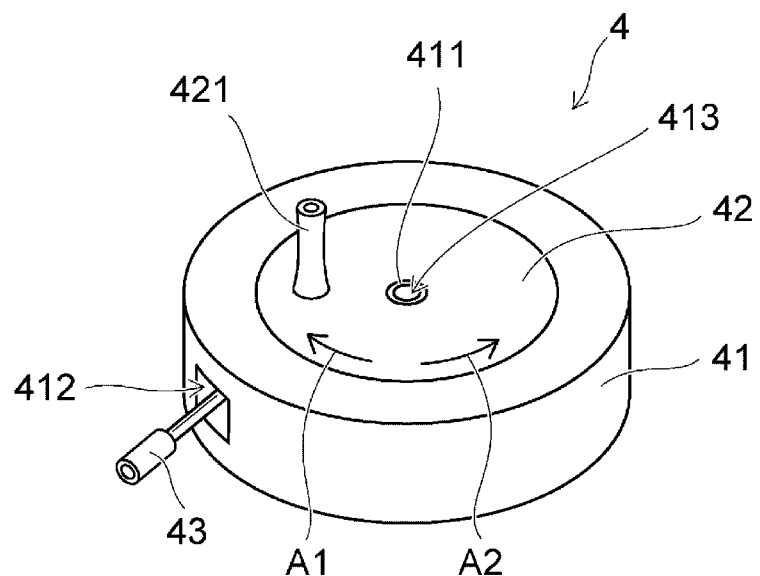
FIG. 3 is a perspective view illustrating a medical assistance device according to a first embodiment of the present disclosure.
Figure 4:
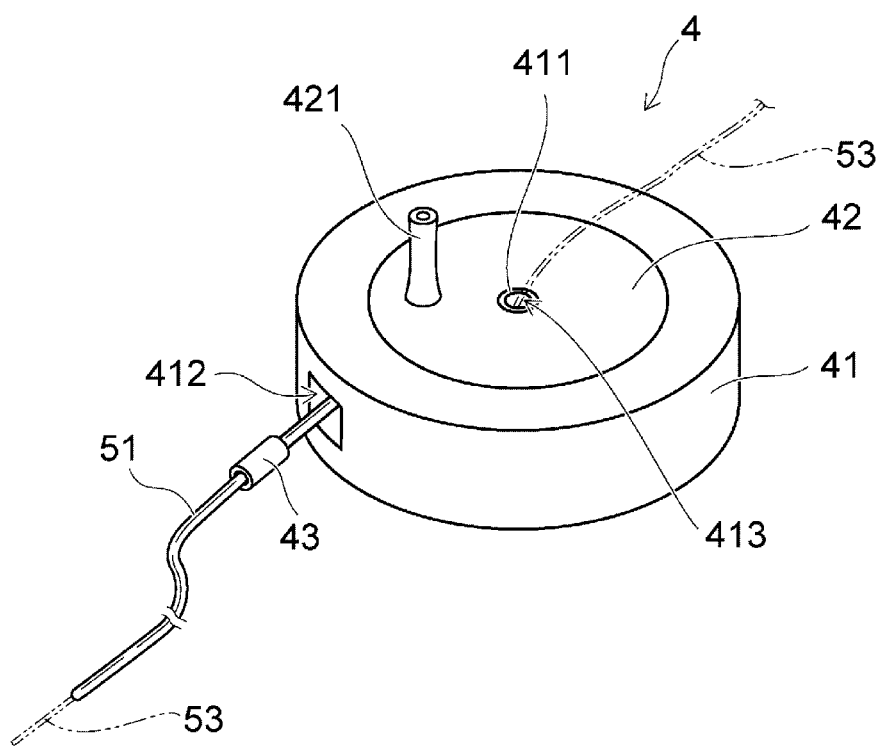
FIG. 4 is a perspective view illustrating the medical assistance device according to the first embodiment of the present disclosure.

FIGS. 3 and 4 are perspective views illustrating a medical assistance device according to a first embodiment of the present disclosure.

Figure 5:
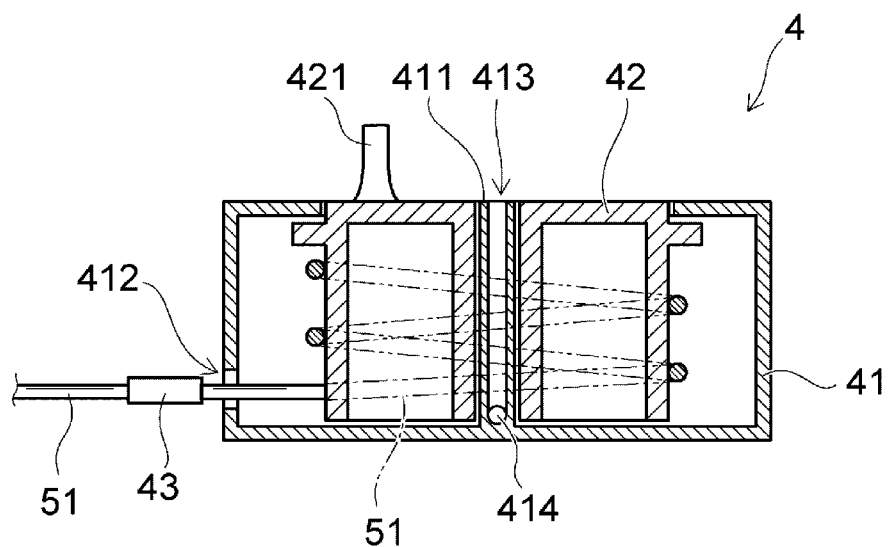
FIG. 5 is a cross-sectional view illustrating an internal structure of the medical assistance device according to the present embodiment.

FIG. 5 is a cross-sectional view illustrating an internal structure of the medical assistance device according to the present embodiment.

Note that FIG. 4 illustrates a state in which another medical device 53 (for example, a guide wire) is inserted into the medical device 51 (for example, a catheter) through an introduction portion 413.

The medical assistance device 4 according to the present embodiment can include a support 41, a winding unit (i.e., length adjustment unit) 42, and a connection section 43.

The support 41 is provided as a main body of the medical assistance device 4 and has a support shaft 411. The support 41 illustrated in FIGS. 3 to 5 has a housing structure in which an internal space is provided. However, the support 41 of the present embodiment is not limited to having an internal space, and the winding unit 42 may be exposed outside the support 41 as long as the winding unit 42 is rotatably supported. The support 41 has an opening portion 412. The connection section 43 is disposed outside the support 41 through the opening portion 412 of the support 41. Note that in a case where most of the winding unit 42 is exposed to the outside of the support 41, the support 41 needs not necessarily have the opening portion 412.

The introduction portion 413 is provided in one end portion of the support shaft 411. A derivation portion 414 is provided in the other end portion of the support shaft 411. The introduction portion 413 is spatially connected to the connection section 43 via an inside of the support shaft 411 and a derivation portion 414. Accordingly, as illustrated in FIG. 4, the surgeon 32 can insert the medical device 53, for example, the guide wire into the connection section 43 through the introduction portion 413 of the support shaft 411, the inside of the support shaft 411, or the derivation portion 414 of the support shaft 411 or can feed a saline for priming into the connection section 43. Note that the introduction portion 413 and the derivation potion 414 are not limited to being provided in the support shaft 411, and may be provided in other portions of the winding unit 42 or in the support 41.

The winding unit 42 is provided to be rotatable about the support shaft 411 of the support 41 with respect to the support 41, as indicated by arrows A1 and A2 illustrated in FIG. 3. Note that the support shaft 411 is not limited to being provided in the support 41, and may be provided in the winding unit 42. That is, the winding unit 42 may be provided rotatably with respect to the support 41 about the support shaft 411 provided in at least one of the support 41 and the winding unit 42. In addition, the support shaft 411 is not limited to being provided in the support 41, and may be provided in the winding unit 41 in the medical assistance devices 4A, 4B, 4C, 4D, 4E, and 4F described later with reference to FIGS. 6 to 10.

In accordance with an aspect, the winding unit 42 has a grip portion 421. The grip portion 421 projects outward from a surface of the winding unit 42 and assists a rotating operation of the winding unit 42. That is, the surgeon 32 or the like can hold and operate the grip portion 421 of the winding unit 42 to rather easily rotate the winding unit 42. Note that the grip portion 421 need not necessarily have a projection portion, and may be, for example, a concave portion into which a finger can be inserted.

As illustrated in FIG. 5, the connection section 43 is provided in the winding unit 42. Specifically, one end portion of the connection section 43 is connected to an outer peripheral portion of the winding unit 42. Therefore, when the winding unit 42 rotates, the connection section 43 rotates along with the winding unit 42 along the outer peripheral portion of the winding unit 42. As illustrated in FIG. 4, the other end portion of the connection section 43 is connected to a proximal portion of the medical device 51. Note that in the present disclosure, a side inserted into a lumen of a living body is referred to as a "distal end" or a "distal side", and a hand side operated by the surgeon is referred to as a "proximal end" or a "proximal side".

A structure and a form of the connection section 43 are not limited. For example, an outer diameter of the connection section 43 may be the same as an outer diameter of a proximal portion of the connected medical device 51 or may be larger or smaller than the outer diameter of the proximal portion of the medical device 51. In addition, the connection section 43 does not necessarily have an elongated body such as a wire or a tube as long as the connection unit 43 is connected to the winding unit 42 and the medical device 51 to connect the winding unit 42 and the medical device 51 to each other via the connection section 43. For example, the connection section 43 may have a structure in which a terminal connectable to the proximal portion of the medical device 51 may be directly fixed to the outer peripheral portion of the winding unit 42.

Next, an operation of the medical assistance device 4 according to the present embodiment will be described.

As illustrated in FIG. 1, the surgeon 32 or the like pulls out the proximal portion of the medical device 51 from the medical device holder 52 and connects the medical device 51 to the connection section 43 of the medical assistance device 4. Then, the surgeon 32 or the like holds the grip portion 421 of the winding unit 42 and rotates the winding unit 42 in a direction of the arrow A1 illustrated in FIG. 3. Accordingly, the connection section 43 rotates together with the winding unit 42 along the outer peripheral portion of the winding unit 42. Therefore, the medical device 51 is pulled out from the medical device holder 52 and wound around the outer peripheral portion of the winding unit 42, as in the medical device 51 illustrated by two-dot chain lines in FIG. 5. When the surgeon 32 or the like uses the medical device 51 connected to the connection section 43, the surgeon 32 or the like can pull the medical device 51 so as to unwind the medical device 51 from the support 41.

According to the present embodiment, in the medical assistance device 4, even in a case where the medical device 51 is relatively long, it is possible to improve the handling and the operation of the medical device 51 by winding the medical device 51. Therefore, it is possible to prevent the medical device 51 from carelessly coming into contact with a dirty area such as the floor of the catheter room 2 or coming into contact with the device installed in the catheter room 2, the patient 31, the surgeon 32, or the like, against the intention of the surgeon 32. Moreover, the surgeon 32 or the like uses the medical assistance device 4 when preparing (startup and setup) the procedure in the biological lumen, and thus, even in the case where the medical device 51 is relatively long, complexity in the startup or setup can be eliminated.

Moreover, the winding unit 42 has the rotationally operable grip portion 421. Accordingly, in a case, for example, where electricity is not provided, the surgeon 32 or the like can operate the grip portion 421 so that the winding unit 42 is rotated to wind the medical 51.

Moreover, as described above, one end portion of the support shaft 411 includes the introduction portion 413 which is spatially connected to the connection section 43. Accordingly, the surgeon 32 or the like can insert another medical device 53 or feed a working fluid through the introduction portion 413. For example, the "working fluid" in the present specification can include, for example, a gas such as air, helium gas, carbon dioxide gas ($CO_2$), and oxygen gas ($O_2$), or a liquid such as a contrast agent, a drug solution, a coating agent, and saline. For example, in a case where the medical device 51 is a catheter, the surgeon 32 or the like can insert the guide wire into a lumen of the catheter through the introduction portion 413. Alternatively, for example, in the case where the medical device 51 is the catheter, the surgeon 32 or the like can feed the saline for priming into the lumen of the catheter through the introduction portion 413.

Note that in the medical assistance device 4 illustrated in FIGS. 3 to 5, the winding unit 42 is provided rotatably with respect to the support 41 about the support shaft 411 extending in a vertical direction. However, an installation form of the winding unit 42 is not limited to the support 41 about the support shaft 411 extending in a vertical direction. For example, the winding unit 42 may be provided rotatably with respect to the support 41 about the support shaft 411 extending in a horizontal direction. The same applies to the medical device 4A described later with reference to FIGS. 6 and 7, and the medical assistance device 4B described later with reference to FIG. 8 in that the support 41 and the support shaft 411 may be vertical or horizontal.

Next, a medical assistance device according to a modification example of the present embodiment will be described.

Note that in a case where components of the medical assistance device 4A according to the present modification example are the same as the components of the medical assistance device 4 according to the present embodiment described above with reference to FIGS. 3 to 5, repeated descriptions are appropriately omitted, and differences between the present embodiment and the present modification will be mainly described.

Figure 6:
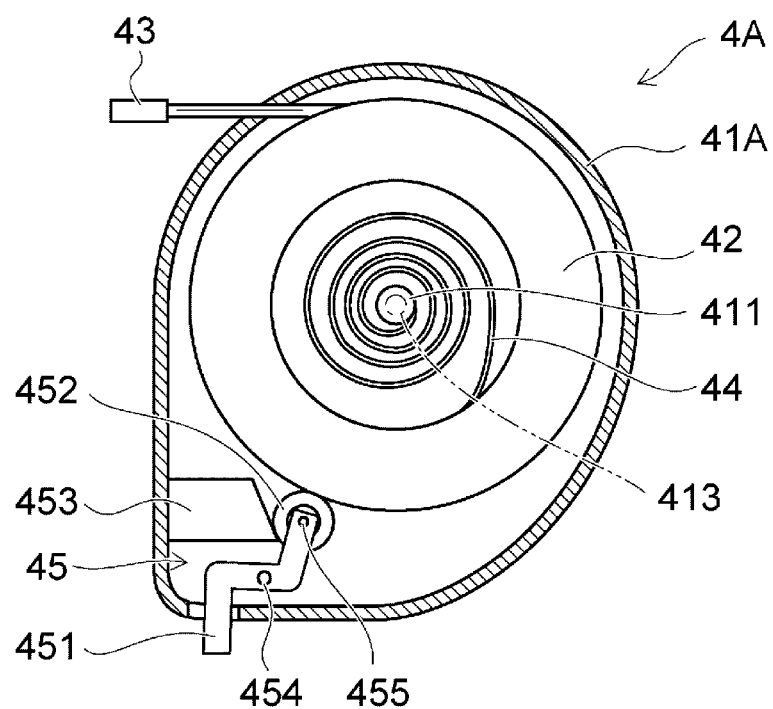
FIG. 6 is a cross-sectional view illustrating a medical assistance device according to a modification example of the present embodiment.
Figure 7:
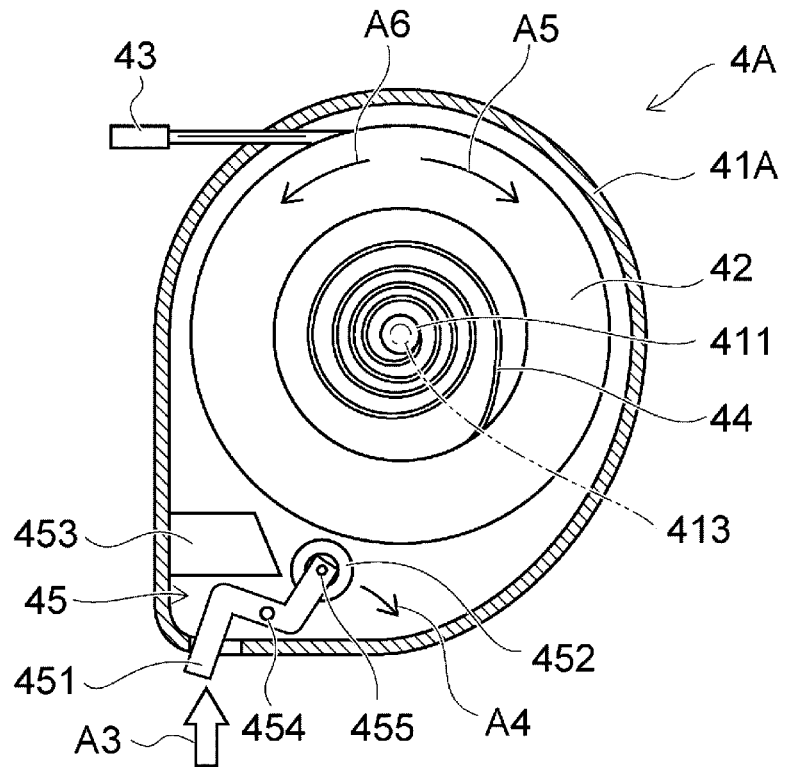
FIG. 7 is a cross-sectional view illustrating the medical assistance device according to the modification example of the present embodiment.

FIGS. 6 and 7 are cross-sectional views illustrating the medical assistance device according to the modification example of the present embodiment.

Note that FIG. 6 is a cross-sectional view illustrating a state where locking of the winding unit is set. FIG. 7 is a cross-sectional view illustrating a state where the locking of the winding unit is released.

The medical assistance device 4A according to the present modification example further includes a biasing unit 44 and a lock mechanism 45 as compared with the medical assistance device 4 described above with reference to FIGS. 3 to 5. The biasing unit 44 is connected to the support shaft 411 of a support 41A and the winding unit 42, and biases the winding unit 42 in a direction (a direction of an arrow A5 illustrated in FIG. 7) in which the medical device 51 is wound. Accordingly, in a case where the surgeon 32 or the like unwinds the medical device 51 connected to the connection section 43 from the support 41A, the surgeon 32 pulls the medical device 51 against a biasing force of the biasing unit 44. For example, the biasing unit 44 can include a mainspring, a leaf spring, or the like.

The lock mechanism 45 can include an operation unit 451, a roller 452, and a pressing portion 453. The operation unit 451 is provided so as to be rotatable about a first shaft 454 provided in the support 41A with respect to the support 41A. Moreover, the operation unit 451 is biased in a direction in which the roller 452 faces the pressing portion 453. As a biasing unit for biasing the operation unit 451 in the direction in which the roller 452 faces the pressing portion 453, for example, a torsion coil spring or the like can be used. The roller 452 is provided in a distal portion of the operation unit 451 so as to be rotatable about a second shaft 455 provided in the operation unit 451 with respect to the operation unit 451. The pressing portion 453 may be fixed to an inner surface of the support 41A.

As illustrated in FIG. 7, a gap between the pressing portion 453 and an outer peripheral portion of the winding unit 42 is narrowed in the biasing direction (the winding direction of the medical device 51, i.e., the direction of the arrow A5) of the biasing unit 44. That is, the gap between the pressing portion 453 and the outer peripheral portion of the winding unit 42 has a wedge shape. Then, in the biasing direction of the biasing unit 44, the gap between the pressing portion 453 and the outer peripheral portion of the winding unit 42 is shorter than an outer diameter of the roller 452.

As illustrated in FIG. 6, in a state where the roller 452 is interposed between the pressing portion 453 and the winding unit 42, the locking of the winding unit 42 can be set. That is, in the state illustrated in FIG. 6, the lock mechanism 45 stops the rotating operation of the winding unit 42 biased by the biasing unit 44. When the operation unit 451 is pushed in a direction of an arrow A3 illustrated in FIG. 7 from the state illustrated in FIG. 6, the operation unit 451 rotates about the first shaft 454 in a direction of an arrow A4 illustrated in FIG. 7. Then, the roller 452 moves away from the pressing portion 453 while rotating about the second shaft 455. Thereby, the locking of the winding unit 42 is released. In the state illustrated in FIG. 7, the winding unit 42 rotates in the direction (the direction of the arrow A5 illustrated in FIG. 7) in which the medical device 51 is wound by the biasing force applied from the biasing unit 44.

As described above, the operation unit 451 is biased in the direction in which the roller 452 faces the pressing portion 453. Therefore, when the force in the direction of the arrow A3 illustrated in FIG. 7 is released from the operation unit 451, the operation unit 451 rotates about the first shaft 454 in a direction opposite to the arrow A4 illustrated in FIG. 7. Then, the roller 452 is interposed again between the pressing portion 453 and the outer peripheral portion of the winding unit 42. Accordingly, the locking of the winding unit 42 is set again.

Next, an operation of the medical assistance device 4A according to the modification example will be described.

As illustrated in FIG. 1, the surgeon 32 or the like pulls out the proximal portion of the medical device 51 from the medical device holder 52 and connects the medical device 51 to the connection section 43 of the medical assistance device 4. Then, when the surgeon 32 or the like pushes the operation unit 451 in the direction of the arrow A3 illustrated in FIG. 7, the winding unit 42 rotates in the direction of the arrow A5 illustrated in FIG. 7 by the biasing force applied from the biasing unit 44. Therefore, the medical device 51 is pulled out from the medical device holder 52 and is wound around the outer peripheral portion of the winding unit 42 (refer to FIG. 5). When the surgeon 32 or the like releases the force pushing the operation unit 451, the roller 452 is interposed between the pressing portion 453 and the outer peripheral portion of the winding unit 42, and thus, the locking of the winding unit 42 is set.

When the surgeon 32 or the like unwinds the medical device 51 connected to the connection section 43 from the support 41A, the surgeon 32 or the like pulls the medical device 51 against the biasing force of the biasing unit 44. Then, the winding unit 42 rotates in a direction of an arrow A6 illustrated in FIG. 7. Accordingly, the operation unit 451 is rotated about the first shaft 454 in the direction of the arrow A4 illustrated in FIG. 7 by a frictional force generated between the roller 452 and the outer peripheral portion of the winding unit 42. Therefore, the roller 452 moves away from the pressing portion 453 while rotating about the second shaft 455. Thereby, the locking of the winding unit 42 is released, and the medical device 51 is unwound from the support 41A.

When the surgeon 32 or the like unwinds the medical device 51 from the support 41A by a required length of the medical device 51 and releases the pulling force of the medical device 51, the winding unit 42 tries to rotate in the direction of the arrow A5 illustrated in FIG. 7 by the biasing force given from the biasing unit 44. In this case, the operation unit 451 is biased in the direction in which the roller 452 faces the pressing portion 453. Accordingly, the operation unit 451 rotates about the first shaft 454 in the direction opposite to the arrow A4 illustrated in FIG. 7. Then, the roller 452 is interposed again between the pressing portion 453 and the outer peripheral portion of the winding unit 42. Thereby, the locking of the winding unit 42 is set again.

According to the medical assistance device 4A of the present modification example, the biasing unit 44 which biases the winding unit 42 in the direction in which the medical device 51 is wound is provided. Accordingly, the winding unit 42 can rather easily wind the medical device 51. Further, even in a case where the winding unit 42 is biased by the biasing unit 44, the lock mechanism 45 can stop the rotating operation of the winding unit 42. Therefore, the surgeon 32 or the like can perform the manipulation with the medical device 51 appropriately bent.

Note that in the present modification, the case where the lock mechanism 45 includes the operation unit 451, the roller 452, and the pressing portion 453 is described as an example. However, the lock mechanism of the present modification example is not limited to the example illustrated in FIGS. 6 and 7. For example, an automatic winding type mechanism may be used, in which when the surgeon 32 or the like pulls the medical device 51, the locking of the winding unit 42 is set, and when the surgeon 32 or the like pulls the medical device 51 again, the locking of the winding unit 42 is released and the winding unit 42 winds the medical device 51.

Next, a medical assistance device according to a second embodiment of the present disclosure will be described.

Note that in a case where components of the medical assistance device 4B according to the second embodiment are the same as the components of the medical assistance device 4 according to the first embodiment described above with reference to FIGS. 3 to 5 and the components of the medical assistance device 4A according to the modification example with reference to FIGS. 6 and 7, repeated descriptions are appropriately omitted, and hereinafter, differences between the components of the medical assistance devices 4, 4A, 4B will be mainly described.

Figure 8:
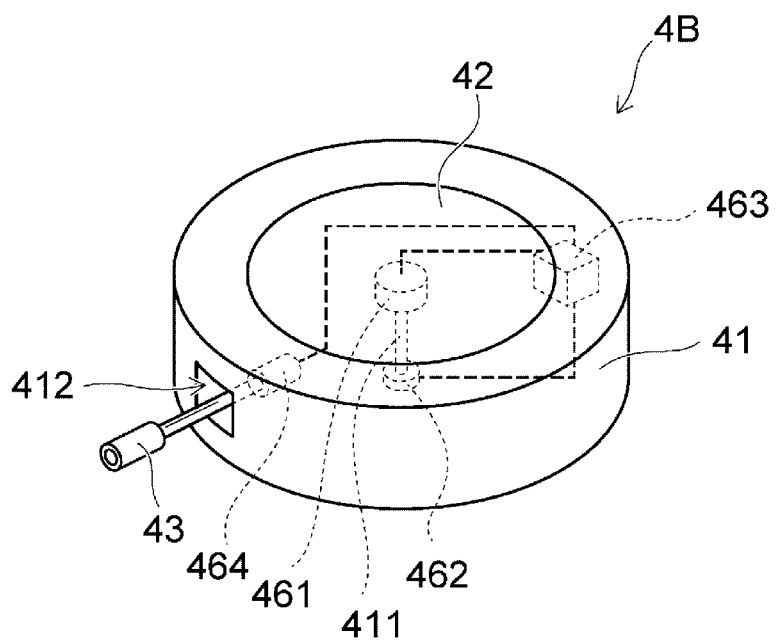
FIG. 8 is a perspective view illustrating a medical assistance device according to a second embodiment of the present disclosure.

FIG. 8 is a perspective view illustrating the medical assistance device according to the second embodiment of the present disclosure.

The medical assistance device 4B according to the present embodiment includes the support 41, the winding unit 42, the connection section 43, a first rotation drive unit 461, a rotation detection unit 462, a control unit 463, and a second rotation drive unit 464. The grip portion 421 described above with reference to FIG. 3 to 5 may or may not be provided. In an example illustrated in FIG. 8, the grip portion 421 is not provided.

The first rotation drive unit 461 is provided in the support 41 and connected to the winding unit 42. When a voltage is supplied to the first rotation drive unit 461, the first rotation drive unit 461 generates a rotation force (first rotation force) for rotating the winding unit 42. The rotation force generated by the first rotation drive unit 461 of the present embodiment corresponds to a "first rotation force" of the present disclosure. For example, the first rotation drive unit 461 is a motor and is connected to the winding unit 42 via a predetermined gear train. The first rotation drive unit 461 is driven based on a control signal transmitted from the control unit 463 to rotate the winding unit 42. In a case where the first rotation drive unit 461 is a stepping motor, the position of the winding unit 42 can be determined with relatively high accuracy.

The rotation detection unit 462 is provided in the support 41 and can detect a rotation angle of the winding unit 42 (i.e., how many times the winding part 42 has been rotated). The rotation detection unit 462 transmits a detection signal regarding the detected rotation angle of the winding unit 42 to the control unit 463. For example, the rotation detection unit 462 can include a rotary encoder, a potentiometer, or the like. Alternatively, as the rotation detection unit 462, a pressure sensor or the like for detecting a torque generated in the winding unit 42 may be used.

The control unit 463 is configured to transmit the control signal to the first rotation drive unit 461 and the second rotation drive unit 464 to control operations of the first rotation drive unit 461 and the second rotation drive unit 464. In addition, the control unit 463 receives the detection signal transmitted from the rotation detection unit 462 to execute a predetermined process.

Specifically, based on the rotation angle of the winding unit 42 detected by the rotation detection unit 462, the control unit 463 can calculate a length of the medical device 51 wound from a predetermined position and a length of the unwound medical device 51. According to this, even in a state where at least a portion of the medical device 51 is wound around the winding unit 42, the surgeon 32 or the like can understand how to take the length of the medical device 51 inserted into the body during the procedure in the biological lumen or a deflection amount (buffer amount) of the medical device 51 based on the length calculated by the control unit 463.

Moreover, when the control unit 463 detects a force in the direction (the direction of the arrow A2 illustrated in FIG. 3) in which the medical device 51 is unwound based on the rotation angle of the winding unit 42 detected by the rotation detection unit 462, the control unit 463 controls the first rotation drive unit 461 to unwind the medical device 51. That is, the control unit 463 controls the first rotation drive unit 461 to rotate the winding unit 42 in the direction (the direction of the arrow A2 illustrated in FIG. 3) in which the medical device 51 is unwound. Meanwhile, when the control unit 463 detects a force in the direction (the direction of the arrow A1 illustrated in FIG. 3) in which the medical device 51 is wound based on the rotation angle of the winding unit 42 detected by the rotation detection unit 462, the control unit 463 controls the first rotation drive unit 461 to wind the medical device 51. That is, the control unit 463 controls the first rotation drive unit 461 to rotate the winding unit 42 in the direction (the direction of the arrow A1 illustrated in FIG. 3) in which the medical device 51 is wound.

According to this, the control unit 463 can control the first rotation drive unit 461 to assist a manipulation or an operation of the surgeon 32 or the like unwinding or winding the medical device 51. Thereby, the medical assistance device 4B according to the present embodiment can support the procedure in the biological lumen.

The second rotation drive unit 464 is provided in the support 41 and is connected to the connection section 43. When a voltage is supplied to the second rotation drive unit 464, the second rotation drive unit 464 generates a rotation force (second rotation force) for rotating the medical device 51 about the axis of the medical device 51. The rotation force generated by the second rotation drive unit 464 of the present embodiment corresponds to a "second rotation force" of the present disclosure. For example, the second rotation drive unit 464 is a motor and is connected to the connection section 43 via a predetermined gear train. The second rotation drive unit 464 is driven based on a control signal transmitted from the control unit 463 to rotate the medical device 51 via the connection section 43. In a case where the second rotation drive unit 464 is a stepping motor, the rotation positions of the connection section 43 and the medical device 51 can be determined with relatively high accuracy.

According to the medical assistance device 4B of the present embodiment, even when the winding unit 42 is not manually operated by the surgeon 32 or the like, a voltage is supplied to the winding unit 42 so that the winding unit 42 can be automatically rotated and can wind the medical device 51.

Moreover, as described above, the second rotation drive unit 464 can rotate the medical device 51 about the axis of the medical device 51 connected to the connection section 43. Accordingly, a choice of the procedure in the biological lumen can be broadened. For example, in a case where the medical device 51 is an image diagnosis catheter (for example, IVUS catheter: Intra Vascular Ultra Sound catheter), the second rotation drive unit 464 rotates the medical device 51 about the axis of the medical device 51 in the biological lumen, and thus, an image of a target lesion can be acquired in a circumferential direction. Alternatively, for example, in a case where the medical device 51 is the guide wire, the second rotation drive unit 464 rotates the medical device 51 about the axis of the medical device 51 in the biological lumen, and thus, it is possible to improve selectivity of a blood vessel in a bifurcated portion of the blood vessel. Further, the same effects as those of the medical assistance device 4 according to the first embodiment described above with reference to FIGS. 3 to 5 can be obtained.

Note that the medical assistance device 4B according to the present embodiment may be connected to an external drive apparatus which holds the medical assistance device 4B and drives the medical assistance device 4B. For example, the external drive apparatus can be interlocked with the medical assistance device 4B to perform forward and pull-back operations of the medical device 51 or rotate the medical device 51 about the axis of the medical device 51.

In the medical assistance device 4B according to the present embodiment, the grip portion 421 described above with reference to FIGS. 3 to 5 may be provided. In a case where the grip portion 421 is provided, the surgeon 32 or the like can rotate the winding unit 42 manually. Further, in this case, a switching unit may be provided, which can switch between a manual mode in which the winding unit 42 is manually rotated by the grip portion 421 and an electric mode in which the winding unit 42 is electrically driven by the first rotation drive unit 461.

Next, a medical assistance device according to a third embodiment of the present disclosure will be described.

Note that in a case where components of the medical assistance device 4C according to the third embodiment are the same as the components of the medical assistance device 4 according to the first embodiment described above with reference to FIGS. 3 to 5 and the components of the medical assistance device 4B according to the second embodiment described above with reference to FIG. 8, repeated descriptions are appropriately omitted, and hereinafter, differences between the components of the medical assistance devices 4, 4A, 4B, 4C will be mainly described.

Figure 9:
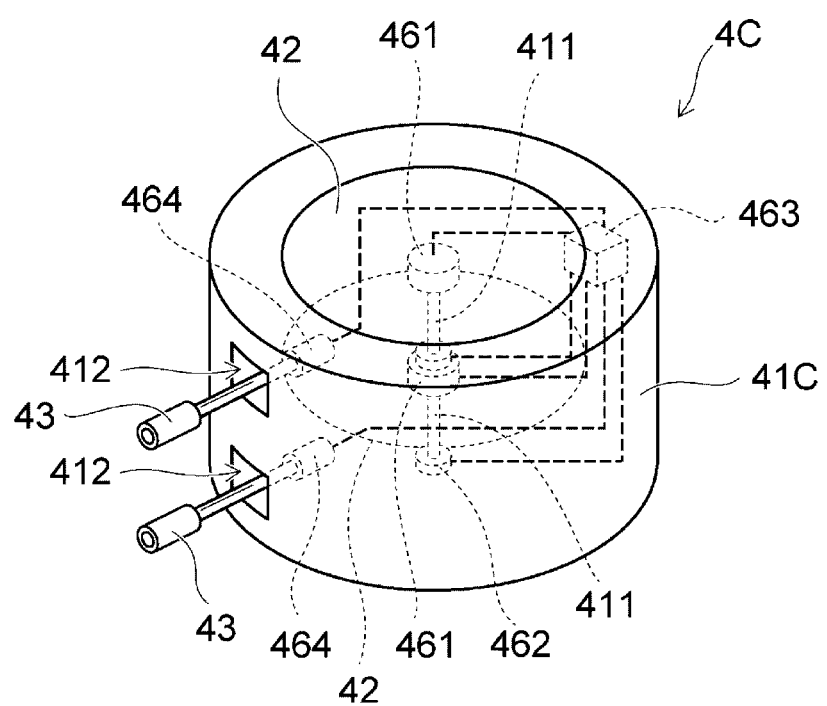
FIG. 9 is a perspective view illustrating a medical assistance device according to a third embodiment of the present disclosure.

FIG. 9 is a perspective view illustrating the medical assistance device according to the third embodiment of the present disclosure.

The medical assistance device 4C according to the present embodiment includes a support 41C, two winding units 42, two connection sections 43, two first rotation drive units 461, two rotation detection units 462, the control unit 463, and two second rotation drive units 464. The two winding units 42 can be rotated independently of each other. For example, the two winding units 42 are provided rotatably with respect to the support 41C about two support shafts 411 disposed coaxially with each other. Alternatively, for example, the two winding units 42 may be provided rotatably with respect to the support 41C about one support shaft 411 common to the two winding units 42.

In accordance with an aspect, one first rotation drive unit 461 is provided in the support 41C and connected to one winding unit 42. When a voltage is supplied to the one first rotation drive unit 461, the first rotation drive unit 461 generates a rotation force (first rotation force) for rotating the one winding unit 42. One rotation detection unit 462 is provided in the support 41C and detects a rotation angle of the one winding unit 42. One second rotation drive unit 464 is provided in the support 41C and is connected to one connection section 43. When a voltage is supplied to the one second rotation drive unit 464, the one second rotation drive unit 464 generates a rotation force (second rotation force) for rotating the medical device 51 about the axis of the medical device 51.

The other first rotation drive unit 461 is provided in the support 41C and connected to the other winding unit 42. When a voltage is supplied to the other first rotation drive unit 461, the other first rotation drive unit 461 generates a rotation force (first rotation force) for rotating the other winding unit 42. The other rotation detection unit 462 is provided in the support 41C and detects a rotation angle of the other winding unit 42. The other second rotation drive unit 464 is provided in the support 41C and is connected to the other connection section 43. When a voltage is supplied to the other second rotation drive unit 464, the other second rotation drive unit 464 generates a rotation force (second rotation force) for rotating the medical device 51 about the axis of the medical device 51.

According to the present embodiment, the two winding units 42 can wind medical devices 51 of different types from each other. For example, in the medical assistance device 4C illustrated in FIG. 9, the one winding unit 42 can wind the catheter. In addition, the other winding unit 42 can wind the guide wire. Accordingly, the choice of the procedure in the biological lumen can be broadened.

As described above, the two winding units 42 can be rotated independently of each other. Accordingly, the control unit 463 individually controls the two first rotation drive units 461 so that the wound lengths and the unwound lengths of the two medical devices 51 can be controlled individually. In addition, the control unit 463 individually controls the two second rotation drive units 464 so that an angle at which each of the two medical devices 51 rotates about the center of the axis can be controlled individually.

Note that in the medical assistance device 4C according to the present embodiment, the two winding units 42 may be fixed to each other. In this case, the two winding units 42 can be rotated in conjunction with each other. Moreover, in this case, one first rotation drive unit 461 and one rotation detection unit 462 may be provided. According to this, the control unit 463 can match the wound lengths of the two medical devices 51 of different types from each other and can match the unwound lengths of the two medical devices 51 of different types from each other. Note that the number of the winding units 42 of the present embodiment is not limited to two winding units 42 and, for example, may be 3 or more winding units 42.

Moreover, in the medical assistance device 4C illustrated in FIG. 9, the two winding units 42 are provided rotatably with respect to the support 41C about the support shaft 411 extending in the vertical direction. However, installation forms of the two winding units 42 are not limited to this. For example, the two winding units 42 may be provided rotatably with respect to the support 41C about the support shaft 411 extending in the horizontal direction. In this case, it is preferable that the two winding units 42 are disposed to be arranged in the horizontal direction, not in an up-down direction.

Next, a medical assistance device according to a fourth embodiment of the present disclosure will be described.

Note that in a case where components of the medical assistance device D according to the fourth embodiment are the same as the components of the medical assistance device 4 according to the first embodiment described above with reference to FIGS. 3 to 5, the components of the medical assistance device 4B according to the second embodiment described above with reference to FIG. 8, and the components of the medical assistance device 4C according to the third embodiment described above with reference to FIG. 9, repeated descriptions are appropriately omitted, and hereinafter, differences between the components of the medical assistance devices 4, 4A, 4B, 4C will be mainly described.

Figure 10:
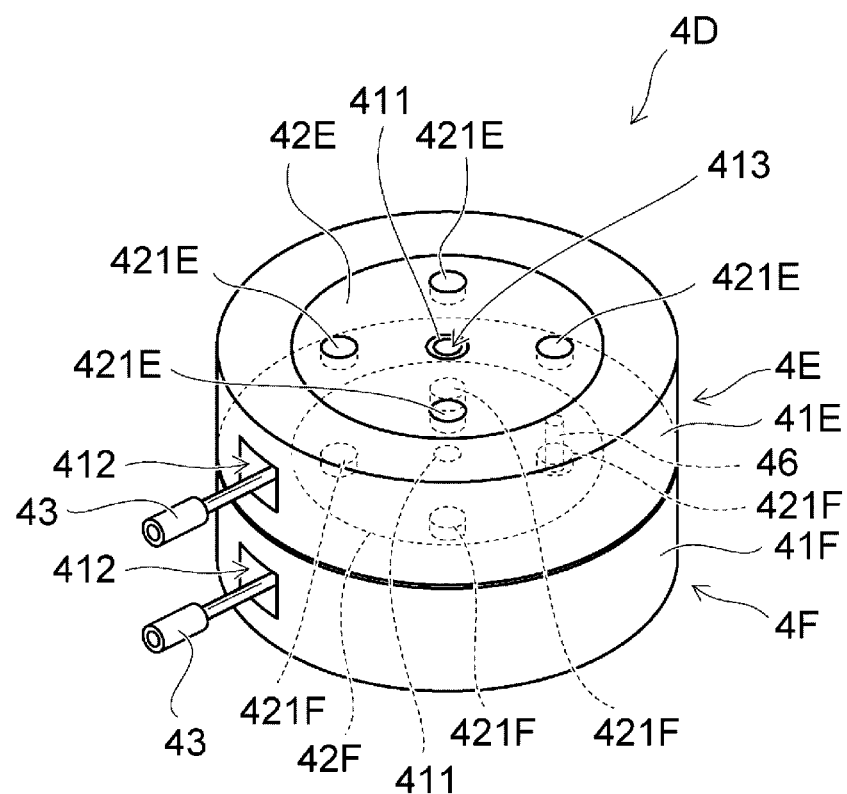
FIG. 10 is a perspective view illustrating a medical assistance device according to a fourth embodiment of the present disclosure.

FIG. 10 is a perspective view illustrating the medical assistance device according to the fourth embodiment of the present disclosure.

The medical assistance device 4D according to the present embodiment has a structure in which a plurality of medical assistance devices are stacked and coupled to each other. In an example illustrated in FIG. 9, two medical assistance devices 4E and 4F are stacked along an axial direction of the support shaft 411 and coupled to each other. The two medical assistance devices 4E and 4F are attachable to and detachable from each other. Note that in the present embodiment, the number of medical assistance devices 4E, 4F to be stacked is not limited to two, and may be three or more medical assistance devices 4E, 4F.

The medical assistance device 4E disposed at a relatively upper stage includes a support 41E, a winding unit 42E, and the connection section 43. The winding unit 42E includes concave portions 421E which are provided on an upper surface of the winding unit 42E. The surgeon 32 or the like inserts a finger into the concave portion 421E of the winding unit 42E so that the winding unit 42E can rotate about the support shaft 411 with respect to the support 41E. A coupling portion 46 protruding downward is provided on a lower surface of the winding unit 42E. The coupling portion 46 is inserted into concave portions 421F of the medical assistance device 4F which is disposed at a relatively lower stage.

The lower-stage medical assistance device 4F includes a support 41F, a winding unit 42F, and the connection section 43. The winding unit 42F includes the concave portions 421F which are provided on an upper surface of the winding unit 42F. The coupling portion 46 which is provided in the winding unit 42E of the upper-stage medical assistance device 4E is inserted into the concave portion 421F.

The coupling portion 46 is fixed to the lower surface of the winding unit 42E, and when the winding unit 42E rotates, the coupling portion 46 rotates about the support shaft 411 with respect to the support 41E together with the winding unit 42E. Accordingly, when the surgeon 32 or the like inserts a finger into the concave portion 421E of the upper-stage medical assistance device 4E and rotates the winding unit 42E, the winding unit 42F of the lower-stage medical assistance device 4F receives a force from the coupling portion 46 inserted into the concave portion 421F and rotates about the support shaft 411 together with the winding unit 42E of the upper-stage medical assistance device 4E. That is, the two winding units 42E and 42F rotate in conjunction with each other.

According to the present embodiment, the two winding units 42E and 42F can wind the medical devices 51 of different types from each other. For example, in the medical assistance device 4D illustrated in FIG. 10, the upper-stage medical assistance device 4E can wind the catheter. In addition, the lower-stage medical assistance device 4F can wind the guide wire. Accordingly, the choice of the procedure in the biological lumen can be broadened. Moreover, even in a case where electricity is not provided, the surgeon 32 or the like rotates the winding unit 42E using the concave portion 421E of the upper-stage winding unit 42E, and thus, can rotate the lower-stage winding unit 42F and can wind the medical devices 51 of different types from each other.

Note that when the surgeon 32 or the like separates the upper-stage medical assistance device 4E and the lower-stage medical assistance device 4F from each other, the upper-stage winding unit 42E and the lower-stage winding unit 42F can rotate independently of each other. In addition, the number of concave portions 421E is not limited to 4 and the number of concave portions 421F is not limited to 4. That is, the number of concave portions 421E may be three or less or may be five or more and the number of concave portions 421F may be three or less or may be five or more.

Moreover, in the medical assistance device 4D illustrated in FIG. 10, the two winding units 42E and 42F are provided rotatably with respect to the supports 41E and 41F about the support shaft 411 extending in the vertical direction. However, installation forms of the two winding units 42E and 42F are not limited to this. For example, the two winding units 42E and 42F may be provided rotatably with respect to the supports 41E and 41F about the support shaft 411 extending in the horizontal direction. In this case, it is preferable that the two winding units 42E and 42F are disposed to be arranged in the horizontal direction, not in the up-down direction. That is, in this case, it may be preferable that the two medical assistance devices 4E and 4F are stacked in the horizontal direction, not in the up-down direction and are coupled to each other.

According to this, the surgeon 32 or the like can rather easily insert their fingers into both the concave portions 421E of the winding unit 42E and the concave portions 421F of the winding unit 42F and can rather easily rotate both the winding unit 42E and the winding unit 42F. Moreover, in this case, each of the two winding units 42E and 42F can have the grip portion 421 (refer to FIG. 3) protruding outward from a surface of the two winding units 42E and 42F. Accordingly, the surgeon 32 or the like can rather easily hold the grip portion 421 which is provided in each of the two winding units 42E and 42F and can rather easily rotate the two winding units 42E and 42F.

Hereinbefore, the embodiments of the present disclosure are described. However, the present disclosure is not limited to the embodiments, and various changes can be made without departing from a scope of claims. The configurations of the embodiments can be partially omitted and can be voluntarily combined so as to be different from the above.

The detailed description above describes embodiments of a medical assistance device which is connected to a medical device used in a procedure in a biological lumen. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A medical assistance device configured to be connected to a medical device, the medical device being configured to be insertable into a biological lumen and used in a procedure in the biological lumen, the medical assistance device comprising:
    a support;
    a winding unit which is rotatably provided about a support shaft with respect to the support and winds the medical device;
    a connection section which is provided in the winding unit, the connection section including one end portion configured to be disposed outside of the support through an opening in the support and connected to a proximal portion of the medical device and another end portion connected to an outer peripheral portion of the winding unit, the connection section configured to rotate along with the winding unit along the outer peripheral portion of the winding unit; and
    a biasing unit which is connected to the support and the winding unit and is constructed to bias the winding unit in a direction in which the medical device is wound.

2. The medical assistance device according to claim 1, wherein the winding unit has a grip portion which is rotationally operated.

3. The medical assistance device according to claim 1, further comprising:
    a lock mechanism which is provided in the support and configured to stop a rotating operation of the winding unit biased by the biasing unit.

4. The medical assistance device according to claim 1, further comprising:
a rotation drive unit which is provided in the support and configured to generate a rotation force for rotating the winding unit when a voltage is supplied to the rotation drive unit.

5. The medical assistance device according to claim 4, further comprising:
a rotation detection unit configured to detect a rotation angle of the winding unit; and
a control unit configured to receive a signal transmitted from the rotation detection unit and configured to calculate a winding length and an unwinding length of the medical device from a predetermined position, based on the rotation angle detected by the rotation detection unit.

6. The medical assistance device according to claim 5, wherein based on the rotation angle detected by the rotation detection unit, the control unit is configured to control the rotation drive unit to unwind the medical device when the control unit detects a force in a direction in which the medical device is unwound, and the control unit is configured to control the rotation drive unit to wind the medical device when the control unit detects a force in a direction in which the medical device is wound.

7. The medical assistance device according to claim 4, wherein the rotation force for rotating the winding unit is a first rotation force;
wherein the rotation drive unit for generating the first rotation force is a first rotation drive unit; and
a second rotation drive unit which generates a second rotation force for rotating the medical device about an axis of the medical device connected to the connection section.

8. The medical assistance device according to claim 1, wherein at least one of the support or the winding unit has an introduction portion which is spatially connected to the connection section and into which another medical device different from the medical device is inserted or a working fluid used at a time of the procedure is fed.

9. A medical assistance device configured to be connected to two or more medical devices, the two or more medical devices configured to be insertable into a biological lumen and used in a procedure in the biological lumen, the medical assistance device comprising:
a support;
two or more winding units, each of the two or more winding units rotatably provided about a support shaft with respect to the support and configured to independently wind one of the two or more medical devices; and
each of the two or more winding units includes a connection section which is provided in a winding unit of the two or more winding units and is connected to one end portion of the medical device, the connection section configured to rotate along with the winding unit along an outer peripheral portion of the winding unit, and a biasing unit which is connected to the support and the winding unit and is constructed to bias the winding unit in a direction in which the medical device is wound.

10. The medical assistance device according to claim 9, further comprising:
two or more rotation drive units, the two or more rotation drive units provided in the support and configured to generate a rotation force for rotating the two or more winding units when a voltage is supplied to the two or more rotation drive units.

11. The medical assistance device according to claim 10, further comprising:
two or more rotation detection units configured to detect a rotation angle of the two or more winding units;
a control unit configured to receive a signal transmitted from the two or more rotation detection units and configured to calculate a winding length and an unwinding length of the two or more medical devices from a predetermined position, based on the rotation angle detected by the two or more rotation detection units; and
wherein based on the rotation angle detected by each of the two or more rotation detection units, the control unit is configured to control each of the two or more rotation drive units to unwind the two or more medical devices when the control unit detects a force in a direction in which the two or more medical devices are unwound, and the control unit is configured to control the two or more rotation drive units to wind the two or more medical devices when the control unit detects a force in a direction in which the two or more medical devices are wound.

12. The medical assistance device according to claim 9, wherein the one end portion of the connection section is configured to be disposed outside of the support through an opening in the support and connected to a proximal portion of the medical device and another end portion connected to the outer peripheral portion of the winding unit.

13. A medical system, the medical system comprising:
one or more medical devices, the one or more medical devices configured to be insertable into a biological lumen and used in a procedure in the biological lumen; and
a medical assistance device, the medical assistance device including a support, a winding unit which is rotatably provided about a support shaft with respect to the support and winds the one or more medical devices, a connection section which is provided in the winding unit, the connection section including one end portion configured to be disposed outside of the support through an opening in the support and connected to a proximal portion of the medical device and another end portion connected to an outer peripheral portion of the winding unit, the connection section configured to rotate along with the winding unit along the outer peripheral portion of the winding unit, and a biasing unit which is connected to the support and the winding unit and is constructed to bias the winding unit in a direction in which the medical device is wound.

14. The medical system according to claim 13, wherein the winding unit of the medical assistance device includes a grip portion which is rotationally operated.

15. The medical system according to claim 13, wherein the medical assistance device further comprises:
a lock mechanism which is provided in the support and configured to stop a rotating operation of the winding unit biased by the biasing unit.

16. The medical system according to claim 13, wherein the medical assistance device further comprises:
a rotation drive unit which is provided in the support and configured to generate a rotation force for rotating the winding unit when a voltage is supplied to the rotation drive unit;
a rotation detection unit configured to detect a rotation angle of the winding unit; and
a control unit configured to receive a signal transmitted from the rotation detection unit and configured to calculate a winding length and an unwinding length of the one or more medical devices from a predetermined position, based on the rotation angle detected by the rotation detection unit.

17. The medical system according to claim 16, wherein based on the rotation angle detected by the rotation detection unit, the control unit is configured to control the rotation drive unit to unwind the one or more medical devices when the control unit detects a force in a direction in which the one or more medical devices are unwound, and the control unit is configured to control the rotation drive unit to wind the one or more medical devices when the control unit detects a force in a direction in which the one or more medical devices are wound.

18. The medical system according to claim 17,
wherein the rotation force for rotating the winding unit is a first rotation force;
wherein the rotation drive unit for generating the first rotation force is a first rotation drive unit; and
a second rotation drive unit which generates a second rotation force for rotating the one or more medical devices about an axis of the one or more medical devices connected to the connection section.

19. The medical system according to claim 13, wherein at least one of the support or the winding unit has an introduction portion which is spatially connected to the connection section and into which another medical device different from the one or more medical devices is inserted or a working fluid used at a time of the procedure is fed.

20. The medical system according to claim 13, wherein the one or more medical devices include a guide wire and/or a catheter.

* * * * *